US010557800B2

(12) United States Patent
Ringlien et al.

(10) Patent No.: US 10,557,800 B2
(45) Date of Patent: Feb. 11, 2020

(54) CALIBRATING INSPECTION DEVICES

(71) Applicant: Owens-Brockway Glass Container Inc., Perrysburg, OH (US)

(72) Inventors: James Ringlien, Maumee, OH (US); William Anderson, Toledo, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 214 days.

(21) Appl. No.: 15/860,369

(22) Filed: Jan. 2, 2018

(65) Prior Publication Data

US 2019/0204239 A1    Jul. 4, 2019

(51) Int. Cl.
| | | |
|---|---|---|
| *G01N 21/00* | (2006.01) | |
| *G01M 11/00* | (2006.01) | |
| *G01N 21/93* | (2006.01) | |
| *G01N 21/90* | (2006.01) | |
| *G01N 21/956* | (2006.01) | |
| *G01B 11/30* | (2006.01) | |
| *G01B 11/25* | (2006.01) | |

(52) U.S. Cl.
CPC ............ *G01N 21/93* (2013.01); *G01B 11/25* (2013.01); *G01B 11/30* (2013.01); *G01N 21/9054* (2013.01); *G01N 21/956* (2013.01)

(58) Field of Classification Search
USPC .................................................. 33/286, 502
See application file for complete search history.

(56) References Cited

U.S. PATENT DOCUMENTS

| | | | | |
|---|---|---|---|---|
| 3,861,807 | A | * | 1/1975 | Lescrenier ........... A61B 6/0457 356/139.07 |
| 4,288,080 | A | * | 9/1981 | Laporte ...................... F41J 7/06 273/406 |
| 4,414,749 | A | * | 11/1983 | Johannsmeier ........... G03F 9/70 33/286 |
| 5,896,195 | A | | 4/1999 | Juvinall et al. |
| 6,025,909 | A | | 2/2000 | Juvinall et al. |
| 6,104,482 | A | | 8/2000 | Brower et al. |
| 6,175,107 | B1 | | 1/2001 | Juvinall |

(Continued)

FOREIGN PATENT DOCUMENTS

| | | |
|---|---|---|
| CN | 105806221 A | 7/2016 |
| JP | 08328624 | 12/1996 |
| JP | 2011220794 | 11/2011 |

OTHER PUBLICATIONS

PCT International Search Report and Written Opinion, Int. Serial No. PCT/US2018/065665, Int. Filing Date: Dec. 14, 2018, Applicant: Owens-Brockway Glass Container Inc., dated: Apr. 11, 2019.

*Primary Examiner* — Shawn Decenzo
*Assistant Examiner* — Jarreas C Underwood

(57) ABSTRACT

An inspection device calibration method includes mounting a laser-operated calibration device to a calibration fixture including an adjustable target having alignment indicia; illuminating the adjustable target with laser light from the calibration device; adjusting the adjustable target to operatively align the alignment indicia with the laser light; removing the calibration device from the calibration fixture; mounting to the calibration fixture, an inspection device including one or more adjustable features; and operating the optical inspection device, including adjusting the inspection device to operatively align the inspection device with the adjustable target.

16 Claims, 4 Drawing Sheets

(56) References Cited

U.S. PATENT DOCUMENTS

| | | | |
|---|---|---|---|
| 6,305,117 B1 * | 10/2001 | Hales, Sr. | F41A 23/02 |
| | | | 42/94 |
| 6,903,814 B1 | 6/2005 | Juvinall et al. | |
| 7,387,039 B1 | 6/2008 | Juvinall et al. | |
| 8,064,049 B2 | 11/2011 | Widera | |
| 8,879,068 B2 | 11/2014 | Hagino et al. | |
| 8,908,148 B2 | 12/2014 | Geraets et al. | |
| 9,275,431 B2 * | 3/2016 | Lin | G06T 7/80 |
| 9,986,233 B1 * | 5/2018 | Curlander | H04N 17/002 |
| 2005/0111004 A1 | 5/2005 | Kim et al. | |
| 2006/0228010 A1 | 10/2006 | Rubbert et al. | |
| 2007/0273894 A1 | 11/2007 | Johnson et al. | |
| 2011/0026014 A1 * | 2/2011 | Mack | G03B 13/22 |
| | | | 356/124 |
| 2015/0130927 A1 | 5/2015 | Luxen et al. | |

* cited by examiner

CALIBRATING INSPECTION DEVICES

TECHNICAL FIELD

The present disclosure relates inspection devices and, more particularly, to calibration of inspection devices.

BACKGROUND

Container manufacturers use inspection devices to ensure the containers they produce meet one or more minimum dimensional standards. Optical inspection devices can use a camera along with one or more mirrors and lasers to measure recently-formed containers. The: optical inspection devices are able to very accurately determine the dimensions of the container. However, the accuracy of the optical inspection devices is largely dependent on how precisely the lasers and mirrors of the optical inspection devices are adjusted. If an optical inspection device measuring container dimensions cannot accurately determine whether the dimensions of containers emerging from production are within an acceptable dimensional range due to improper adjustment, manufacturers may needlessly continue to produce non-conforming containers and ship those containers to customers.

The optical inspection devices can be individually adjusted in situ. But individual adjustment of each optical inspection device made by different people using different criteria may create undesirable variations between different devices. When a plurality of those optical inspection devices is used to inspect containers, different criteria may be used to determine whether or not containers conform to the acceptable dimensional range. It would be helpful to ensure that the optical inspection devices are accurately aligned and calibrated to a standard so that each device consistently detects when containers are outside of acceptable dimensional ranges.

SUMMARY OF THE DISCLOSURE

In one embodiment, an inspection device calibration method includes mounting a laser-operated calibration device to a calibration fixture including an adjustable target having alignment indicia; illuminating the adjustable target with laser light from the calibration device; adjusting the adjustable target to operatively align the alignment indicia with the laser light; removing the calibration device from the calibration fixture; mounting to the calibration fixture an inspection device, including one or more adjustable features; and operating the inspection device, including adjusting the inspection device to operatively align the inspection device with the adjustable target.

In another embodiment, a calibration fixture for adjusting inspection devices includes a tower having one or more attachments that releasably secure a calibration device or an inspection device in a fixed position relative to an adjustable target; and the adjustable target, located adjacent to the tower, including alignment indicia and one or more releasable fasteners that permit movement of the adjustable target when the calibration device is mounted to the tower and prevent movement of the adjustable target when the inspection device is mounted to the tower.

In yet another embodiment, a calibration device used with a calibration fixture includes one or more attachments that releasably secure the calibration device to the calibration fixture; a first fixed x-axis laser generating a first x-axis beam that impinges on an adjustable target of the calibration fixture; a second fixed x-axis laser generating a second x-axis beam that impinges on the adjustable target of the calibration fixture; and a y-axis laser generating a y-axis beam substantially perpendicular to the first x-axis beam and the second x-axis beam that impinges on the adjustable target of the calibration fixture.

BRIEF DESCRIPTION OF THE DRAWINGS

The disclosure may best be understood from the following description, the appended claims, and the accompanying drawings, in which:

DETAILED DESCRIPTION

Inspection devices can be adjusted using a calibration fixture that accurately and consistently guides adjustment of the lasers, mirrors, and lenses of optical inspection devices. The calibration fixture can include one or more mounting points used to position optical inspection devices relative to an adjustable target. When, for example, optical container neck finish inspection devices are mounted to the calibration fixture, the orientation of laser beams from the calibration device onto the adjustable target, or the appearance of the adjustable target to the camera of the optical inspection devices, or both can be used to indicate whether or not the optical inspection devices are properly calibrated including alignment.

Before using the calibration fixture to align and adjust optical inspection devices, a calibration device can be attached to the calibration fixture to ensure that the adjustable target of the calibration fixture is properly positioned with respect to the mounting point(s). The attached calibration device directs a plurality of lasers toward the adjustable target. The plurality of lasers provides laser light pathways that duplicate light pathways of the inspection laser and a pathway of incoming light to the inspection camera. Depending on where the lasers impinge upon the adjustable target, a user can determine whether or not the adjustable target of the calibration fixture is properly positioned for calibrating optical inspection devices. If not properly positioned, the user can move the adjustable target in the x- and z-directions until the lasers visually indicate that the target is properly positioned. After the adjustable target has been properly positioned, it can be secured in a fixed position before the optical inspection device(s) are attached to the calibration fixture. The calibration device can then be detached from the calibration fixture and the calibration fixture is ready to calibrate optical inspection devices.

An optical inspection device can then be attached to the mounting point(s) of the calibration fixture and a can calibrate the optical inspection device including alignment thereof. The camera and laser(s) of the optical inspection device may be directed at the adjustable target of the calibration fixture. A pattern of the inspection laser light impinging on the adjustable target may indicate how to adjust the camera, laser(s), lens(es), and/or mirror(s) of the optical inspection device, if needed.

Figure 1A:
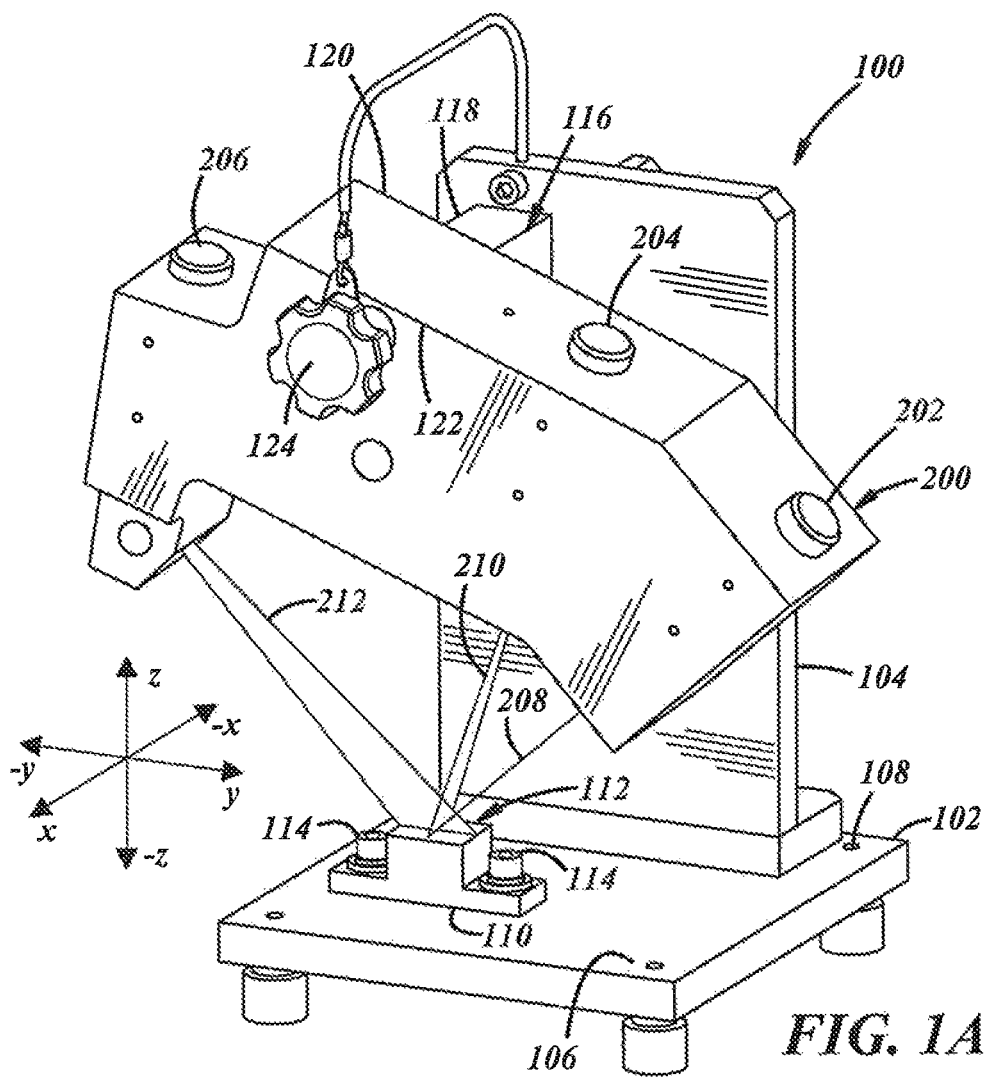
FIG. 1A is a perspective view of an illustrative embodiment of a calibration fixture and a calibration device.
Figure 1B:
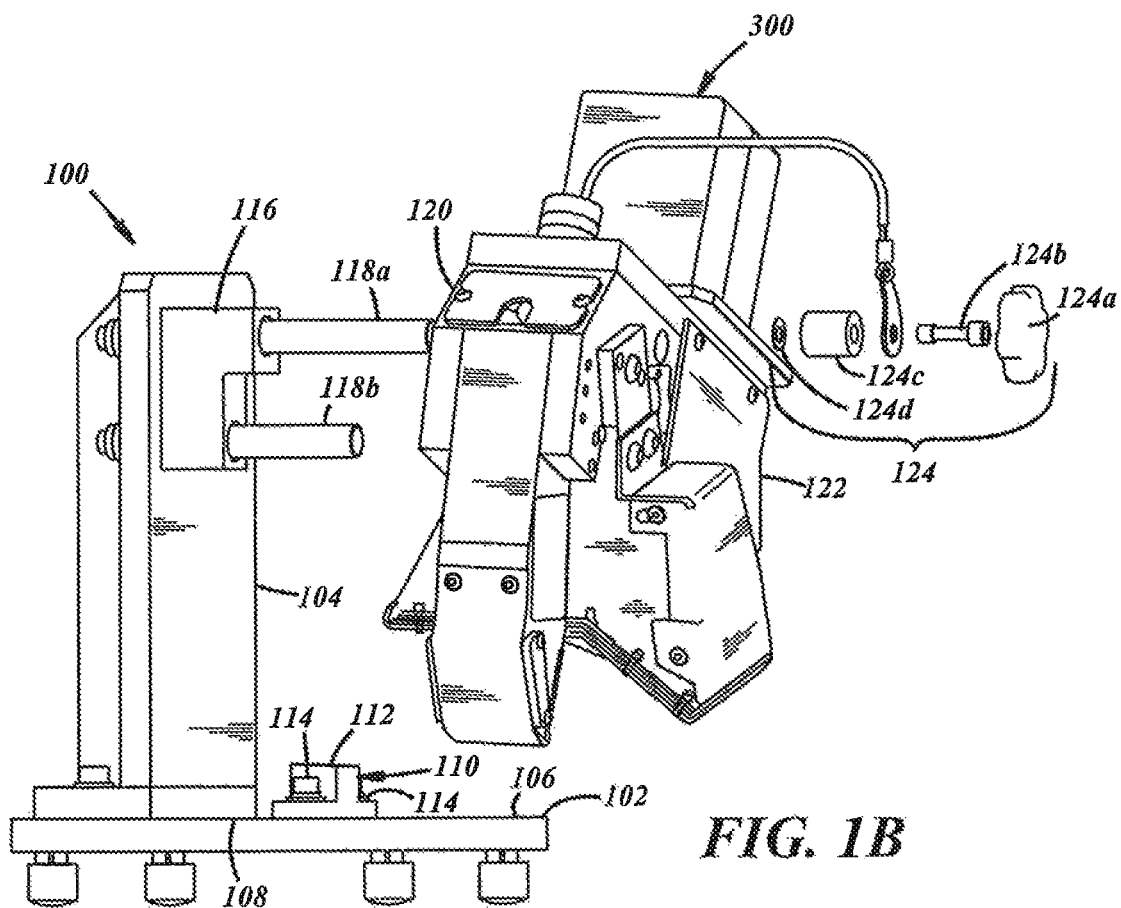
FIG. 1B is a perspective view of an illustrative embodiment of a calibration fixture and an optical inspection device.

Turning to FIGS. 1A and 1B, exemplary embodiments of a calibration fixture 100 are shown with a calibration device 200 and an optical inspection device 300. The calibration fixture includes a base 102 supporting a tower 104 that is mounted to a surface 106 of the base 102. The tower 104 can be rigidly mounted to the base 102 at a base end 108 so that the tower 104 supports the calibration device 200 above the surface 106. In this implementation, the tower 104 is mounted so that the base 102 is substantially perpendicular to the tower 104. An adjustable target 110 may be mounted on the surface 106 of the base 102 adjacent to the tower 104. A target surface 112 of the adjustable target 110 can face the calibration device 200 and include adjustment indicia in the form of cross hairs in the x- and y-directions for positioning the adjustable target 110, although alternative adjustment indicia may be used. The adjustable target 110 can be moved in three different directions relative to the surface 106. In this implementation, two releasable fasteners 114 can be released permitting the movement of the adjustable to 110 in the x- and y-directions. The releasable fasteners 114 can be thumbscrews, cam-actuated studs, cap screws, or other similar devices. The adjustable target 110 may be moved along the z-axis either closer to or further from the calibration device 200 by inserting one or more shims (not shown) in between the surface 106 and the adjustable target 110. A plurality of shims can be provided for this purpose, each having the same or different thicknesses. When used alone or in various combinations, the shims can provide an appropriate height in the z-direction to appropriately calibrate the adjustable target 110 with respect to the calibration device 200.

The calibration device 200 is removably attached to the calibration fixture 100 to align the adjustable target 110. The calibration device 200 can include a plurality of lasers that are trusted to have been previously aimed such that the adjustable target 110 can be moved relative to these lasers and then fixed and used to adjust other devices such as an optical inspection device 300. A first x-axis laser 202, a second x-axis laser 204, and a y-axis laser 206 are shown. Each of the lasers 202, 204, and 206 can generate a beam of light that impinges the adjustable target 110 to create straight lines of light against the target surface 112 that, when the adjustable target 110 is properly aligned, can be collinear with the cross hairs on the target surface 112. A first x-axis beam 208, a second x-axis beam 210, and a y-axis beam 212 are shown as linear beams of light traversing at least a portion of the target surface 112. The process of aligning the adjustable target 110 relative to the laser beams 208, 210, and 212 will be discussed in more detail below.

The calibration fixture 100 can include an attachment 115, such as a mounting block, having a base 118, and two locating posts 118a and 118b fixed to the tower 104 that may extend from one side 120 of the calibration device 200 to another side 122 of the calibration device 200 that is opposite the side 120 when the calibration device 200 is mounted to the calibration fixture 100 (as shown in FIG. 1B). An attachment assembly 124 can include a knob 124a, a screw 124b, a sleeve 124c, and a retainer 124d. The calibration device 200 can be slid over the two locating posts 118a, 118b until the side 120 of the calibration device 200 contacts the base 118. In this implementation, the attachment 116 is shown to include a plurality of tubular supports that are stepped such that the supports have different lengths. The plurality of supports can connect the calibration device 200 with the tower 104 to prevent torsional movement of the calibration device 200 with respect to the tower 104 about the attachment 116. However, it should be understood that other implementations are possible using a single point of attachment 116, such as a single tubular support. The longer (upper) locating post 118a can include an internal (female) thread that receives the male thread of a screw 124b. The sleeve 124c may fit over the screw 124b and be retained by the retainer 124d to keep the attachment assembly 124 attached to the calibration fixture 100. The screw 124b may include am internal (female) thread at an end opposite the male thread. The knob 124a, or a thumbscrew with a threaded male stud may then be attached to the screw 124b via the internal thread and the knob 124a can rigidly and securely hold the base 118 so that it securely abuts the side 120 of the calibration device 200. This can fixedly hold the calibration device 200 relative to the adjustable target 110. Although the foregoing describes one method of mounting the calibration device 200 to the calibration fixture 100, tongue-and-groove configurations, dovetail configurations, or any other arrangements suitable for holding the calibration device 200 may be used. The base 118 and optional mounting points can provide datum points relative to winch the adjustable target 110 is adjusted.

Generally speaking, a user can loosen the thumbscrews 114 allowing the insertion of one or more shims (not shown) between the surface 106 and the adjustable target 110. Different shims or combinations of shims can be placed between the surface 106 and the adjustable target 110 until a calibrated amount of height is added along the z-axis to provide an appropriate distance between the adjustable target 110 and the calibration device 200. The adjustable target 110 may still be moved in the x- and y-direction after correcting for the height of the target in the z direction. Once the adjustable target 110 is aligned in the x- and y-direction, the thumbscrews 114 can be tightened.

Turning to FIGS. 2-5, an implementation of a portion of a method of calibrating an inspection device is shown. In this portion of the method, the adjustable target 110 of the calibration fixture 100 can be calibrated using the calibration device 200. The method begins by mounting the laser-operated calibration device 200 to the calibration fixture 100 as is described above and illuminating the adjustable target 110 with the first x-axis laser beam 208, the second x-axis, laser beam 210, and the y-axis laser beam 212. The adjustable target 110 includes alignment indicia, as the cross hairs indicated by -x and y-axes, that may be used to direct movement of the adjustable target 110 thereby configuring the calibration fixture 100 so that it can be used to calibrate optical inspection devices. FIGS. 2-5 depict plan news of the target surface 112 of the adjustable target 110 in various positions relative to the calibration device 200 and how the laser beams 208, 210, and 212 impinge on the surface 112 in each position.

Figure 2:
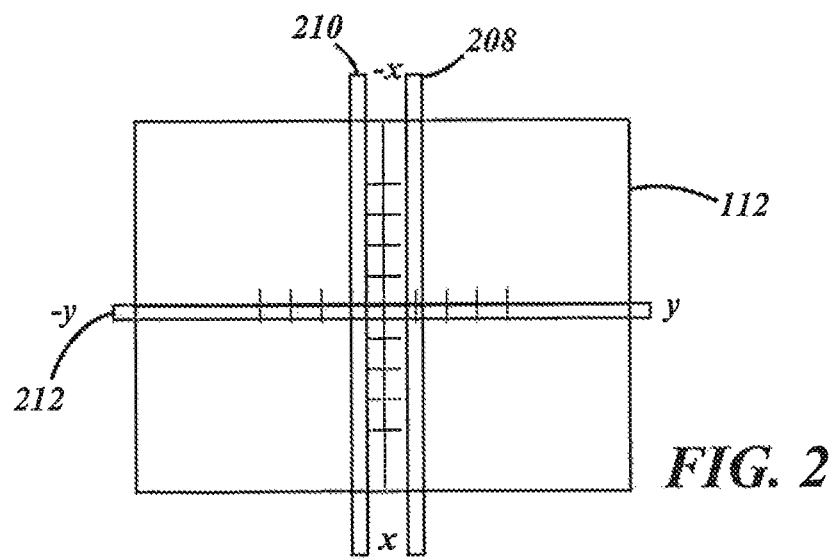
FIG. 2 is a plan view of an illustrative embodiment of an adjustable target indicating when the adjustable target is too close to a calibration device.
Figure 3:
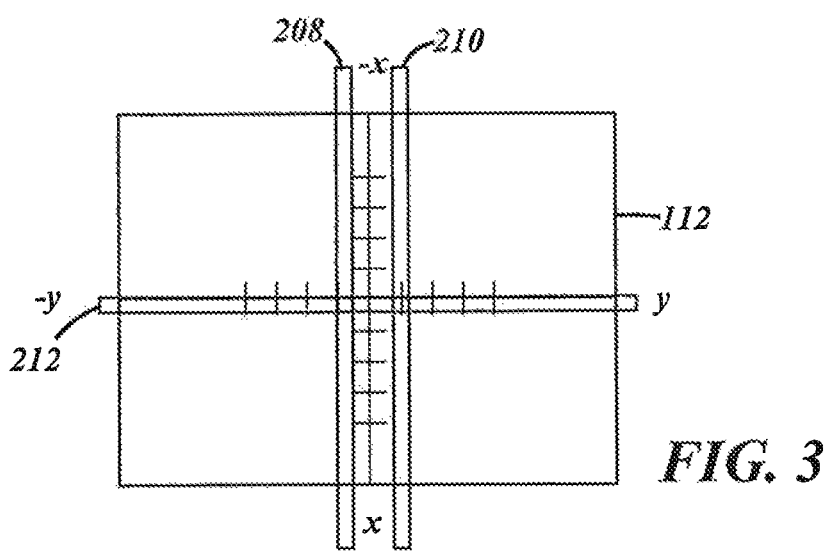
FIG. 3 is a plan view of an illustrative embodiment of an adjustable target indicating when the adjustable target is too far away from a calibration device.

With respect to FIG. 2, a plan view of the target surface 112 is shown when the adjustable target 110 is too close to the calibration device 200. In this example, the distance between the target surface 112 and the calibration device 200 along the z-axis is too small. The laser beams 208, 210, and 212 and the target surface 112 can convey this condition when the first x-axis beam 208 appears on the positive side of the y-axis and the second x-axis beam 210 appears on the negative side of the y-axis. This arrangement of the laser beams can indicate to a user that shims should be removed under the adjustable target 110 to move the target surface 112 farther from the calibration device 200. Conversely, FIG. 3 depicts another plan view of the target surface 112 when the adjustable target 110 is too far away from the calibration device 200. In this example, the distance between the target surface 112 and the calibration device 200 along the z-axis is too great. The laser beams 208, 210, and 212 and the target surface 112 can convey this condition when the first x-axis beam 208 appears on the negative side of the y-axis and the second x-axis beam 210 appears on the positive side of the y-axis. This arrangement of the laser beams can indicate to a user that shims should be added to bring the target surface 112 closer to the calibration device 200.

Figure 4:
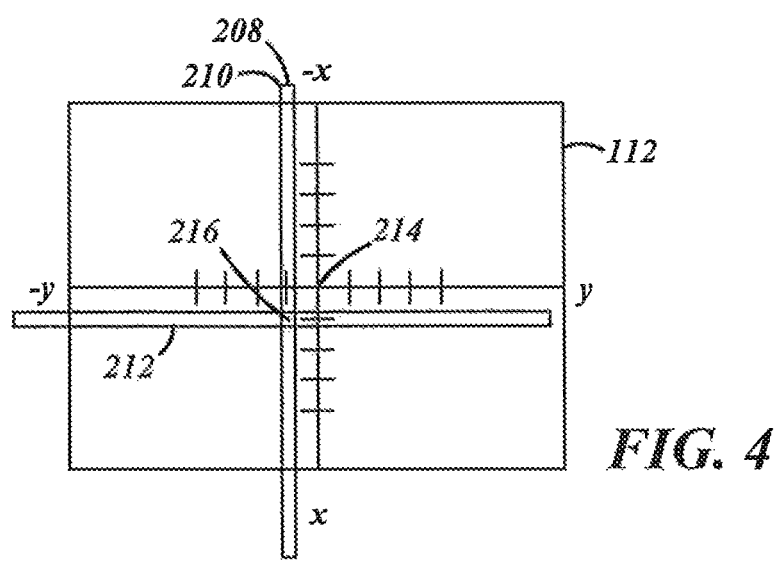
FIG. 4 is a plan view of an illustrative embodiment of an adjustable target indicating when the adjustable target is the correct height relative to a calibration device but offset from the calibration device.
Figure 5:
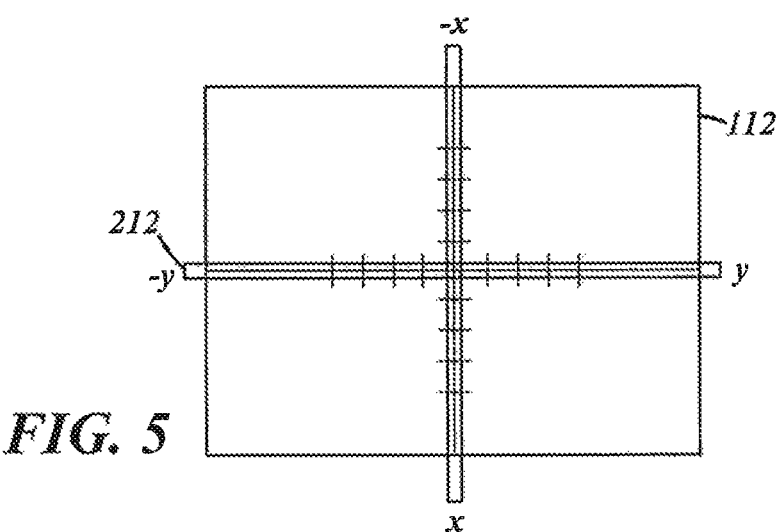
FIG. 5 is a plan view of an illustrative embodiment of an adjustable target indicating when the adjustable target been successfully adjusted with a calibration device.

FIGS. 4-5 depict additional plan views of the target surface 112 when the adjustable target 110 is the correct distance from the calibration device 200 measured along the z-axis. However, with respect to FIG. 4, the laser beams 208, 210, and 212 indicate that the adjustable target 110 is not properly aligned in the x-y plane. The overlapping impingement of the first x-axis laser beam 208 and the second x-axis laser beam 210 may indicate the proper height of the adjustable target 110. But the center point 214 of the cross hairs is offset from the center point 216 of the laser beams 208, 210, and 212. While the thumbscrews 114 are loosened, the user can move the adjustable target 110 until the center point 214 overlaps center point 216. In this example, the user can move the center point 214 in the positive x direction and the negative y direction. FIG. 5 depicts a plan view of the target surface 212 and the laser beams 208, 210, 212 when the adjustable target 110 is properly aligned. As shown, the overlapping impingement of the first x-axis laser beam 208 and the second x-axis laser beam 210 indicates the proper height of the adjustable target 110, and the center point 214 of the cross hairs is centered in the center point 216 of the laser beams 208, 210, 212 and the x-axis and y-axis laser beams are parallel to and aligned on the cross hairs of the target (i.e. the x-axis and y-axis laser beams are not at an oblique angle to the cross hairs). When the user achieves what is shown in FIG. 5, the thumbscrews 114 can be tightened to secure the adjustable target 110 against movement. The calibration device 200 can then be removed from the calibration fixture 100 by removing the knob 124. The calibration device 200 can then be slid off of the threaded stud away from the tower 104 and the target is positioned in the calibration fixture 100 to receive, and align and otherwise calibrate the optical inspection device 300 including alignment thereof.

While the target surface 112 and the surface 106 of base 102 are shown in FIGS. 1-5 as planes that are parallel in relationship to each other, it should be understood that the target surface 112 need not have this relationship to the base 102. Other implementations are possible in which the target surface 112 is substantially perpendicular to the base 102 or the target surface 112 can be oriented in a variety of other positions with respect to the base 102.

Figure 6:
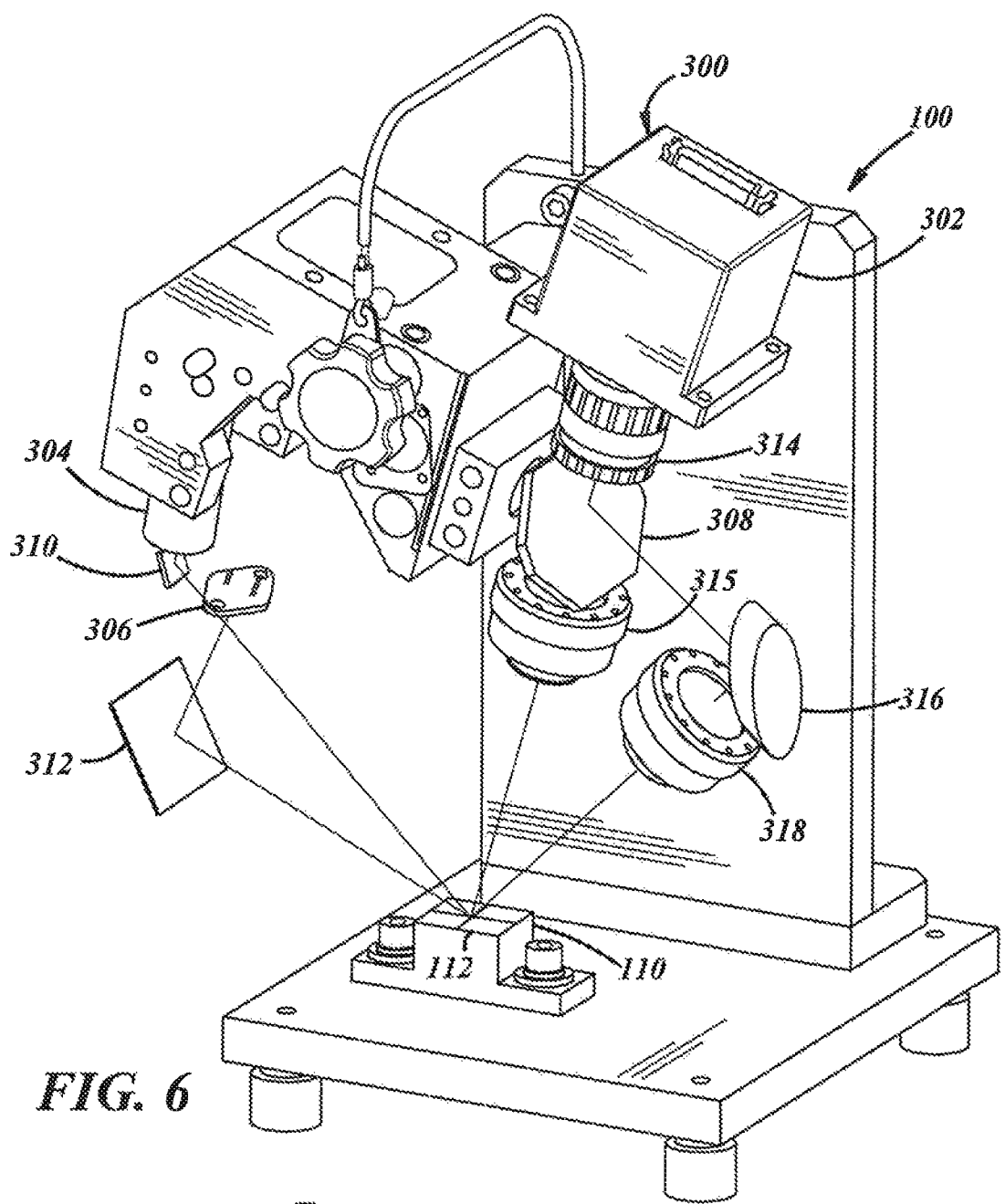
FIG. 6 is a perspective view of an illustrative embodiment of a calibration fixture and an optical inspection device.

Turning to FIG. 6, an implementation of another portion of a method of calibrating an inspection device is shown. This portion of the method involves adjusting one or more optical inspection devices using the calibration fixture 100 after its adjustable target 110 has been aligned and otherwise calibrated using the calibration device 200. In this implementation, an embodiment of an optical inspection device 300 is shown mounted to the calibration fixture 100. The optical inspection device 300 can be mounted to the calibration fixture 100 using the same steps used to mount the calibration device 200 that are described above. The optical inspection device 300 may be used to measure one or more dimensions of a container and may include a camera 302. A wire edge laser 304 and a crizzle LED 306 each generating light that ultimately impinges on the adjustable target 110 may also be included with the optical inspection device 300. The images received at the camera 302 can be superimposed on each other by a camera beam splitter 308 while the light generated by the wire edge laser 304 and crizzle LED 306 can be directed by a wire edge laser mirror 310 and crizzle minor 312, respectively. A wire edge image mirror 316 can receive an image of the wire edge laser 304 reflected off of the target surface 112. The camera 302 may include a camera lens 314 that filters light and focuses an image on the image sensor of the camera 302. The optical inspection device 300 may also include a wire edge lens 318 positioned between the adjustable target 110 and the wire edge laser mirror 310 for focusing an image ultimately received by the camera 302 before it reaches the beam splitter 308. The optical inspection device 300 may also include a crizzle lens 315 positioned between the adjustable target 110 and the beam splitter 308 for focusing an image ultimately received by the camera 302 before reaching the beam splitter 308.

Figure 8:
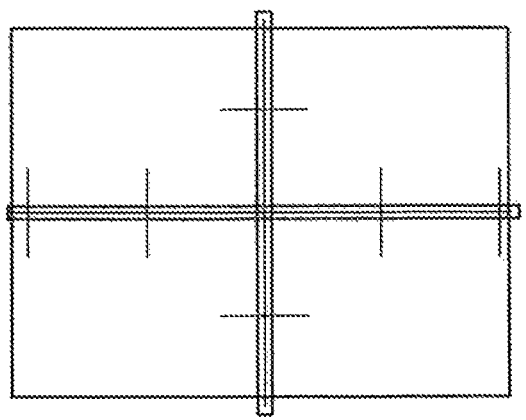
FIG. 8 is a plan view of an illustrative embodiment of an adjustable target indicating when the adjustable target is correctly aligned relative to a calibration device.
Figure 7:
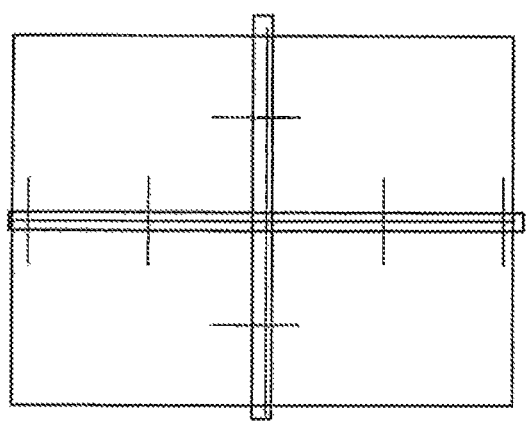
FIG. 7 is a plan view of an illustrative embodiment of an adjustable target indicating when the adjustable target is out of alignment relative to a calibration device.

The camera, lasers, mirrors, and lenses of the optical inspection device 300 can all be adjusted as part of aligning and otherwise calibrating the optical inspection device 300. The method of calibrating the optical inspection device 300 can begin by setting the camera lens 314 to infinity and then adjusting the focus of the camera lens 314 until the target surface 112 comes into sharp focus. The wire edge laser mirror 310 can be adjusted to align the laser beam generated by the wire edge laser 304 on the alignment indicia of the target surface 112. Next, the wire edge image mirror 316 can be adjusted until an image of the wire edge laser 304 sent from the wire edge laser mirror 310 and received by the camera 302 is superimposed on the image of the wire edge laser 304 received directly at the camera 302 from the target surface 112 as shown in FIGS. 1-8. FIG. 7 depicts an asymmetrical offset between the alignment indicia and the laser beams while FIG. 8 depicts a device in alignment. The wire edge lens 318 may then be focused to sharpen the image of the wire edge laser 304 reflected off of the wire edge laser mirror 310 and the target surface 112 of the adjustable target 110 as it is reflected to the camera 302 via the wire edge image mirror 316 and the beam splitter 308. The crizzle mirror 312 can be adjusted to center light from the crizzle LED 306 on the cross hairs of the target surface 112. The optical inspection device 300 may then be considered aligned and otherwise calibrated and can be removed from the attachment 116 in the same way that the calibration device 200 had been previously removed from the calibration fixture 100.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) win become apparent to those skilled in the art. All such other embodiments, changes, and modifications are intended to come within the scope of the appended claims. For instance, many other optical inspection devices can be used with different calibration fixtures other than the ones expressly disclosed. In one example, U.S. Pat. No. 6,175,107 to John W. Juvinall discloses an apparatus for inspecting a container that can be used with the disclosed calibration fixture apparatus; the patent is incorporated by reference herein in its entirety.

As used in this specification and claims, the terms "e.g.," "for example," "for instance," "such as," and "like," and the verbs "comprising," "having", "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. An inspection device calibration method, comprising:
   mounting a laser-operated calibration device to a calibration fixture including an adjustable target having alignment indicia;
   illuminating the adjustable target with laser light from the calibration device;
   adjusting the adjustable target to operatively align the alignment indicia with the laser light;
   removing the calibration device from the calibration fixture;
   mounting to the calibration fixture an inspection device including one or more adjustable features; and
   operating the inspection device, including adjusting the inspection device to operatively align the inspection device with the adjustable target.

2. The method of claim 1, further comprising removing the inspection device from the calibration fixture and inspecting containers using the inspection device.

3. The method of claim 1, wherein the alignment indicia includes crosshairs.

4. The method of claim 3, wherein the adjusting step comprises adjusting the adjustable target to operatively align laser lines with the crosshairs.

5. The method of claim 1, wherein the mounting steps include using a common mounting point of the calibration fixture to locate both the calibration device and the inspection device.

6. The method of claim 5, wherein the mounting steps include using one or more additional mounting points along with the common mounting point of the calibration fixture to locate both the calibration device and the inspection device.

7. The method of claim 1, wherein the adjustable target is three-dimensionally adjustable along x-, y-, and z-axes.

8. The method of claim 1, wherein the operating step comprises focusing camera lens of the inspection device on the adjustable target.

9. The method of claim 1, wherein the operating step comprises adjusting a wire edge laser mirror of the inspection device to align a wire edge laser beam on the adjustable target.

10. The method of claim 1, wherein the operating step comprises adjusting a wire edge image mirror of the inspection device to superimpose an image of a wire edge laser at a camera.

11. The method of claim 1, wherein the operating step comprises focusing a wire edge lens of the optical inspection device to sharpen an image at a camera.

12. The method of claim 1, wherein the operating step comprises adjusting a crizzle light emitting diode (LED) of the inspection device to center light from the crizzle LED on the adjustable target.

13. The method of claim 1, wherein adjusting the adjustable target comprises moving the adjustable target along a z-axis closer to or further from the calibration device.

14. The method of claim 13, wherein adjusting the adjustable target comprises inserting one or more shims between a base of the calibration fixture and the adjustable target.

15. The method of claim 13, wherein the adjusting step comprises moving the adjustable target along the z-axis farther from the calibration device when a first x-axis laser beam impinges a target surface of the adjustable target along a positive y-axis of the alignment indicia and a second x-axis laser beam impinges the target surface of the adjustable target along a negative y-axis of the alignment indicia.

16. The method of claim 13, wherein the adjusting step comprises moving the adjustable target along the z-axis nearer to the calibration device when a first x-axis laser beam impinges a target surface of the adjustable target along a negative y-axis of the alignment indicia and a second x-axis laser beam impinges the target surface of the adjustable target along a positive y-axis of the alignment indicia.

\* \* \* \* \*